(12) United States Patent
Kaushal et al.

(10) Patent No.: US 8,512,323 B2
(45) Date of Patent: Aug. 20, 2013

(54) DEVICES AND METHODS FOR COMPUTER-ASSISTED SURGERY

(75) Inventors: Shalesh Kaushal, Worcester, MA (US); Michael Darnall Furman, Cambridge (GB); Thomas Bryan Demarse, Gainesville, FL (US); Jennifer Delight Simonotto, Newcastle upon Tyne (GB)

(73) Assignee: University of Florida Research Foundation, Inc., Gainesville, FL (US)

( * ) Notice: Subject to any disclaimer, the term of this patent is extended or adjusted under 35 U.S.C. 154(b) by 968 days.

(21) Appl. No.: 12/440,766

(22) PCT Filed: Sep. 12, 2007

(86) PCT No.: PCT/US2007/078284
§ 371 (c)(1),
(2), (4) Date: Sep. 8, 2009

(87) PCT Pub. No.: WO2008/033933
PCT Pub. Date: Mar. 20, 2008

(65) Prior Publication Data
US 2009/0318911 A1 Dec. 24, 2009

Related U.S. Application Data

(60) Provisional application No. 60/843,983, filed on Sep. 12, 2006.

(51) Int. Cl.
*A61B 18/18* (2006.01)
*A61B 3/10* (2006.01)
*G06K 9/00* (2006.01)

(52) U.S. Cl.
USPC .......................................................... 606/13

(58) Field of Classification Search
USPC ........ 606/2–29; 351/205–206, 208; 382/128
See application file for complete search history.

(56) References Cited

U.S. PATENT DOCUMENTS

| 5,568,208 | A | 10/1996 | Van de Velde |
| 6,006,126 | A | 12/1999 | Cosman |
| 6,247,812 | B1 | 6/2001 | Miehle et al. |

(Continued)

FOREIGN PATENT DOCUMENTS

| EP | 0 391 376 | 1/1996 |
| EP | 1 602 321 | 12/2005 |

(Continued)

OTHER PUBLICATIONS

Stewart et al., "The Dual-Bootstrap Iterative Closest Point Algorithm with Application to Retinal Image Registration," *IEEE Transactions on Medical Imaging*, Nov. 2003, vol. 22, pp. 1379-1394.

*Primary Examiner* — Dawayne A Pinkney
(74) *Attorney, Agent, or Firm* — Saliwanchik, Lloyd & Eisenschenk (57) ABSTRACT

Disclosed are devices and methods for correlating or aligning pre-surgical image(s) with image(s) observed during a surgical procedure to aid in orientation of tissues and devices for performing a surgical procedure. In a preferred embodiment, the invention provides devices and methods for aligning pre-surgical image(s) of optical tissues or structures, e.g., the retina, with real-time images observed or obtained with a slit lamp, or other optical viewing device. The ability of the subject invention to correlate these images can advantageously provide the physician with greater accuracy when administering surgical treatment, such as with a laser, and can significantly reduce surgery time.

14 Claims, 10 Drawing Sheets

(56) References Cited

U.S. PATENT DOCUMENTS

| | | | |
|---|---|---|---|
| 6,339,446 B1* | 1/2002 | Miyoshi | 348/65 |
| 6,575,969 B1 | 6/2003 | Rittman, III et al. | |
| 7,261,414 B2* | 8/2007 | Saigusa et al. | 351/208 |
| 7,331,667 B2 | 2/2008 | Grotehusmann et al. | |
| 2002/0151781 A1* | 10/2002 | Ohishi et al. | 600/407 |
| 2004/0073455 A1* | 4/2004 | McConnochie et al. | 705/2 |
| 2007/0008725 A1* | 1/2007 | Luther et al. | 362/257 |
| 2008/0009669 A1* | 1/2008 | Ozawa et al. | 600/101 |
| 2008/0033301 A1 | 2/2008 | DellaVecchia et al. | |

FOREIGN PATENT DOCUMENTS

| | | |
|---|---|---|
| EP | 1 767 174 | 3/2007 |
| WO | WO 2004/043234 | 5/2004 |
| WO | WO 2008/150331 | 12/2008 |

* cited by examiner

DEVICES AND METHODS FOR COMPUTER-ASSISTED SURGERY

CROSS-REFERENCE TO A RELATED APPLICATION

This application is a National Stage Application of International Application Number PCT/US2007/078284, filed Sep. 12, 2007; which claims the benefit of U.S. Provisional Application No. 60/843,983, filed Sep. 12, 2006, both of which are incorporated herein by reference in their entirety.

BACKGROUND OF THE INVENTION

Lasers are an established treatment for numerous ophthalmic pathologies and disorders. The use of lasers, however, requires precise beam size and accurate placement during surgery to prevent damage to surrounding tissues and sufficient exposure to the affected area. Thus, surgical pre-planning is often conducted to ensure accuracy and treatment of the proper tissues.

To assist in pre-planning, physicians often obtain a pre-surgical image, such as fluoroscein image, of the pertinent ocular structure, for example, the eye retina. Utilizing the pre-surgical image, one or more physicians can formulate a surgical plan for treatment, which usually includes the placement of one or more fiducial marks. Such fiducial marks aid the physician in orienting devices and tissues during surgery. During actual surgical treatment, a slit lamp, or other optical viewing device, is used to observe the pertinent ocular structure while administering treatment.

Frequently, a slit lamp, or other optical viewing device, integrated with a mechanically- or computer-controllable laser, is used to observe the eye structure(s) in real-time and administer laser treatment. During such procedures, a physician often refers to the pre-surgical image and the associated fiducial marks to correlate points in the current view of the eye structure(s) to guide the laser pointer or "aiming dot." This process of correlation usually requires a physician to repeatedly refer to the pre-surgical image and the image observed by the optical viewing device. The need for a physician to direct attention towards more than one image during a procedure can result in errors, including treating the wrong area, insufficient treatment of an area, or missing a target.

There exists a need to correlate one or more pre-surgical tissue or structure images with real-time tissue or structure images that does not require a physician to separately view or monitor two or more images. The ability to correlate images and reduce or eliminate the need for physicians to view or monitor more than one image can increase surgical accuracy and reduce surgery time.

BRIEF SUMMARY

The subject invention provides devices and methods for correlating one or more pre-surgical static images with real-time images obtained during a surgical procedure to aid in orientation of tissues and devices for performing a surgical procedure. In particular, the subject invention provides devices and methods for correlating static pre-surgical tissue or structure images with real-time tissue or structure images. More particularly, the invention provides devices and methods for correlating static pre-surgical images of optical tissues or structures, e.g., the retina, with real-time images or observations obtained with a slit lamp, or other optical viewing device.

The ability of the subject invention to correlate these multiple images can advantageously provide the physician with greater accuracy when administering surgical treatment, such as with a laser, and can significantly reduce surgery time.

In one embodiment, a pre-surgical image of a retina, for example a fluorescein image, is displayed simultaneously with the real-time view of the same retina, as seen through a slit lamp, or other viewing device without enhancements. In a further embodiment, the images are overlapping. And, in a still further embodiment, the images are overlapping and correlated such that one image is precisely aligned over the other. With this combined image, a physician can more accurately determine the appropriate treatment area(s) during a procedure.

In another embodiment, the subject invention utilizes a video camera optically connected to a slit lamp, or other optical viewing device, to capture real-time images of a retina. A static pre-surgical image of the same retina can be projected on the same monitor. By adjusting the position of the video camera, the two images can be matched or correlated. In a further embodiment, each image can be separately controlled, such that one or the other can be partially or completely dimmed from the monitor view. For example, once the images are correlated, a physician can alter the images or eliminate the real-time image and administer treatment based upon the pre-surgical image, which can include, for example, fiducial marks, position indicators, and/or tissue viewing enhancements (dyes, radiation, etc.).

In a still further embodiment, the images can be correlated during a procedure by using a computer and software capable of making corrections to the image correlations to compensate for random or unexpected movement. In a preferred embodiment, the images are correlated during a procedure using a computer and software capable of making relatively rapid image correlations to compensate for random or unexpected movement.

In another preferred embodiment, a video-camera, optically connected to a slit lamp, can be used to observe a real-time image of a retina on a computer monitor, including any indicators displayed on the retina, such as a laser aiming dot. A pre-surgically prepared fluorescein retinal angiogram of the same retina is displayed simultaneously on the same monitor. A computer with appropriate software can be used to correlate the images using features on the fluorescein retinal angiogram that correspond to features seen through the slit lamp.

BRIEF DESCRIPTION OF DRAWINGS

FIG. 1 (prior art)—illustrates an example of a current method and devices for most optical surgery procedures. In this example, the surgeon performing a retinal laser surgery procedure views a real-time image of the retina through an optical viewing device, such as a slit lamp. However, in order to determine accurately where to direct the laser beam, the surgeon must visually correlate the current view of the retina with a previously obtained static fluorescein image of the same retina. Fiducial marks can be placed on the fluorescein image prior to surgery to assist the physician. Once a precise point has been determined, the surgeon can manually position the laser beam, for example, with a laser aiming dot.

FIG. 2—illustrates an embodiment of the method of the subject invention and devices for performing optical surgical procedures. In this example, the real-time view of the retinal image is captured from an optical viewing device, such as a slit lamp. This real-time image is overlaid by a previously obtained static fluorescein image of the same retina and both images are simultaneously displayed on a screen or monitor. Fiducial marks can also be viewed on the screen or monitor to assist the physician. In this embodiment, the laser beam can be either manually controlled or computer controlled.

FIG. 3C—is a photograph of an embodiment of the slit lamp shown in FIG. 3. The photograph shows an enlarged view of the left side to show details of an uncovered secondary observation port. In one embodiment of the subject invention, a video camera can be attached to a secondary observation port to capture and display the image seen through the slit lamp.

DETAILED DISCLOSURE

The subject invention provides devices and methods for correlating at least one static pre-surgical image with at least one image viewed or observed during a surgical procedure. The ability to correlate or align said images can aid in orientation of tissues and devices for performing a surgical procedure.

In particular, the subject invention provides devices and methods for correlating or aligning static pre-surgical tissues or structure images with real-time tissue or structure images. More particularly, the invention provides devices and methods for correlating or aligning at least one pre-surgical image of optical tissue or structure with at least one real-time image observed with a slit lamp, or other optical viewing device.

The subject invention is particularly useful in the field of optical surgical procedures, in particular retinal laser surgeries. However, a person with skill in the art would readily recognize other uses for the devices and methods of the subject invention. While the subject application exemplifies a use for optical retinal laser surgery, other applications apparent to a person with skill in the art and having benefit of the subject disclosure are contemplated to be within the scope of the present invention.

The term "patient" as used herein, describes an animal, including mammals, to which the systems and methods of the present invention are provided. Mammalian species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary or tracking purposes.

With reference to the attached figures that show certain embodiments of the subject invention, it can be seen that the subject invention comprises in general a slit lamp 20, or other optical viewing device, capable of viewing tissues or structures, such as, for example, an eye retina with an attached video camera, or other device capable of capturing real-time images or observations. In one embodiment, a video camera 30 can be connected to at least one secondary observation port 22 of a slit lamp 20. However, any of a variety of devices and techniques can be used to capture and display the images observed through a slit lamp. For example, a video camera, or like device, could be coupled directly to the eye-piece of the slit lamp 20, such that the view of the retina is observed on a secondary display device such as a monitor, screen, etc.

Figure 2:
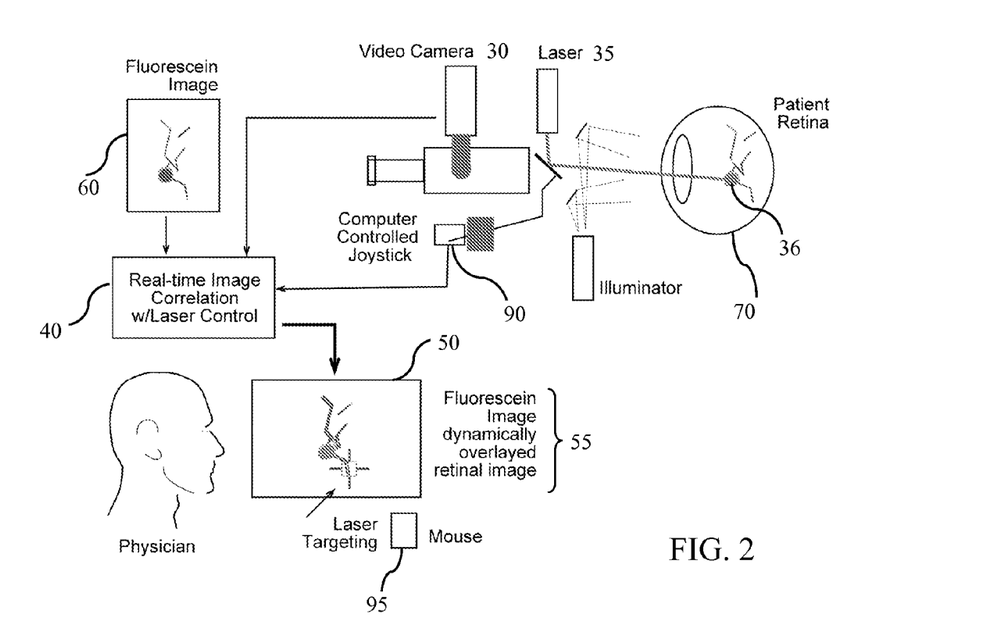
Figure 3A:
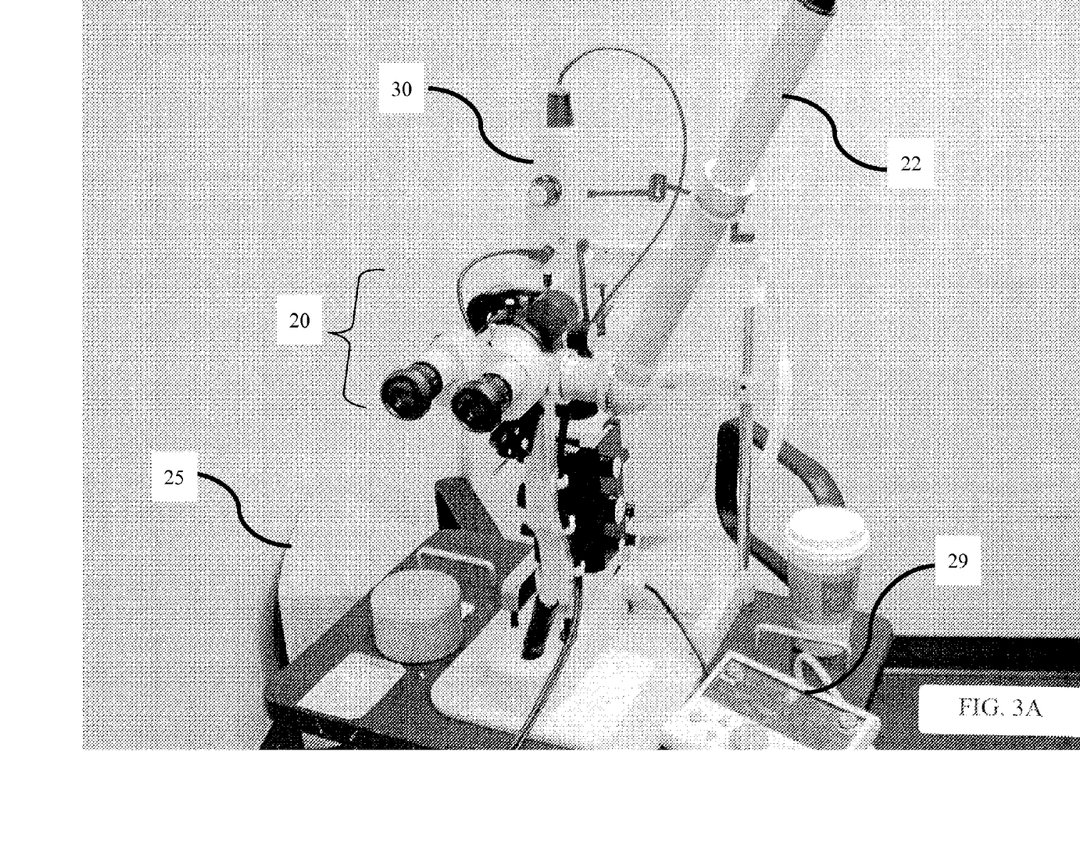
FIG. 3A and 3B—are photographs of an embodiment of a typical slit lamp with an attached secondary observer tube and laser device, as viewed from the front or eye-piece side (FIG. 3A) and from the right side (FIG. 3B). For the subject invention, the secondary observer tube can be removed from the slit lamp observation port and a video camera affixed thereto to capture and display the view from the slit lamp.
Figure 3B:
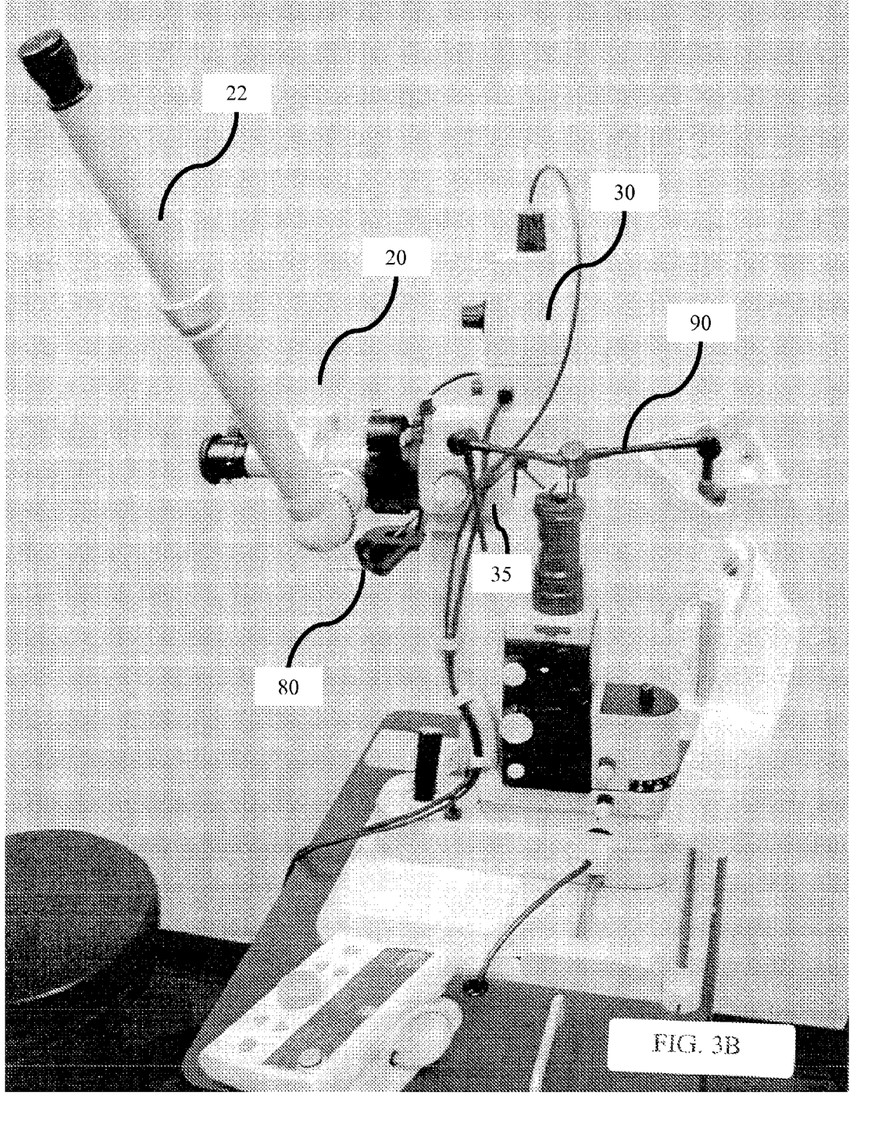
Figure 3C:
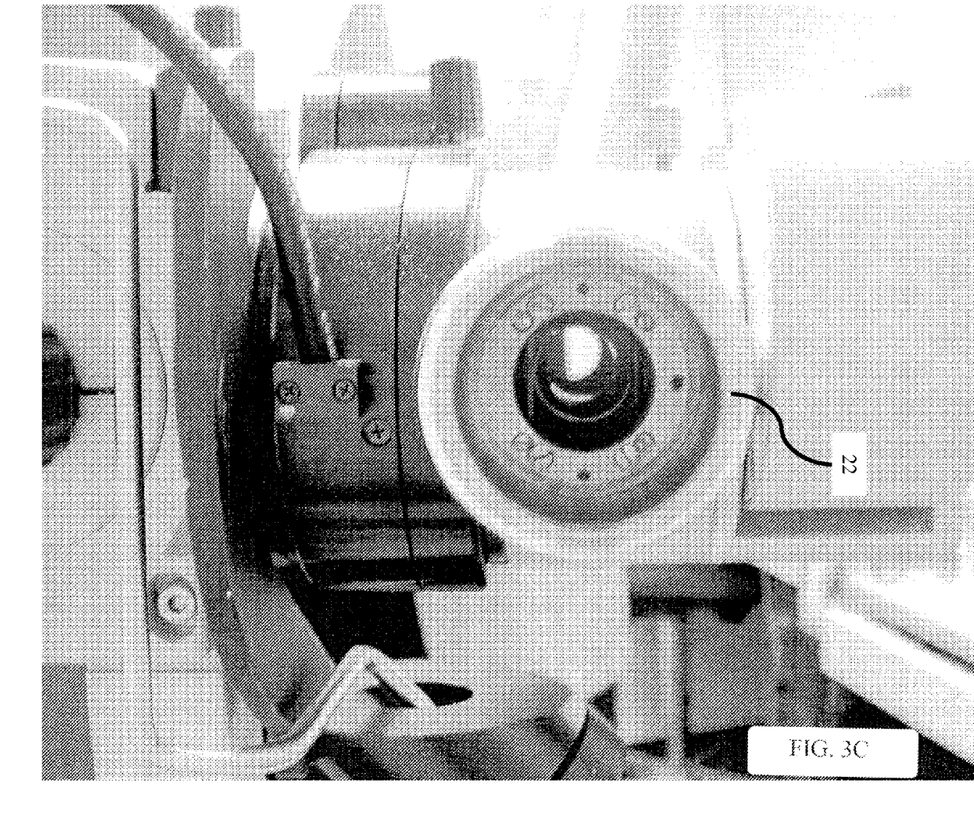
Figure 4A:
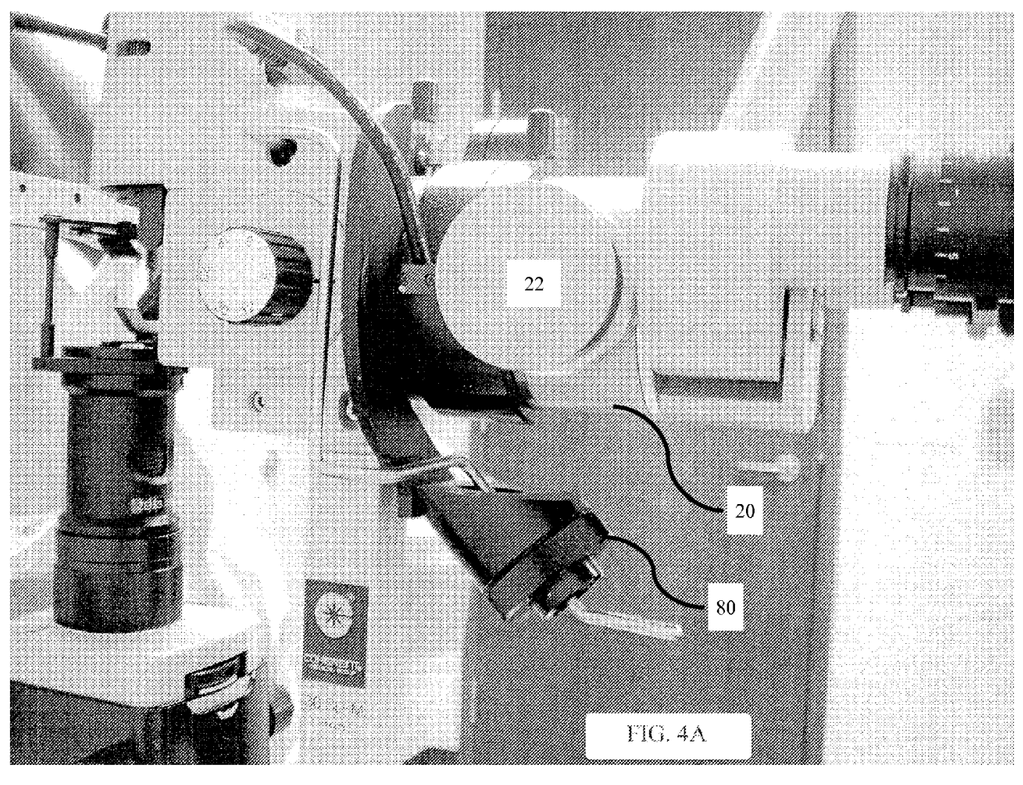
FIG. 4A—is a photograph of the left side view of the slit lamp shown in FIG. 3, enlarged to show the details of one embodiment of a "joy stick" for controlling the laser connected to the slit lamp.
Figure 4B:
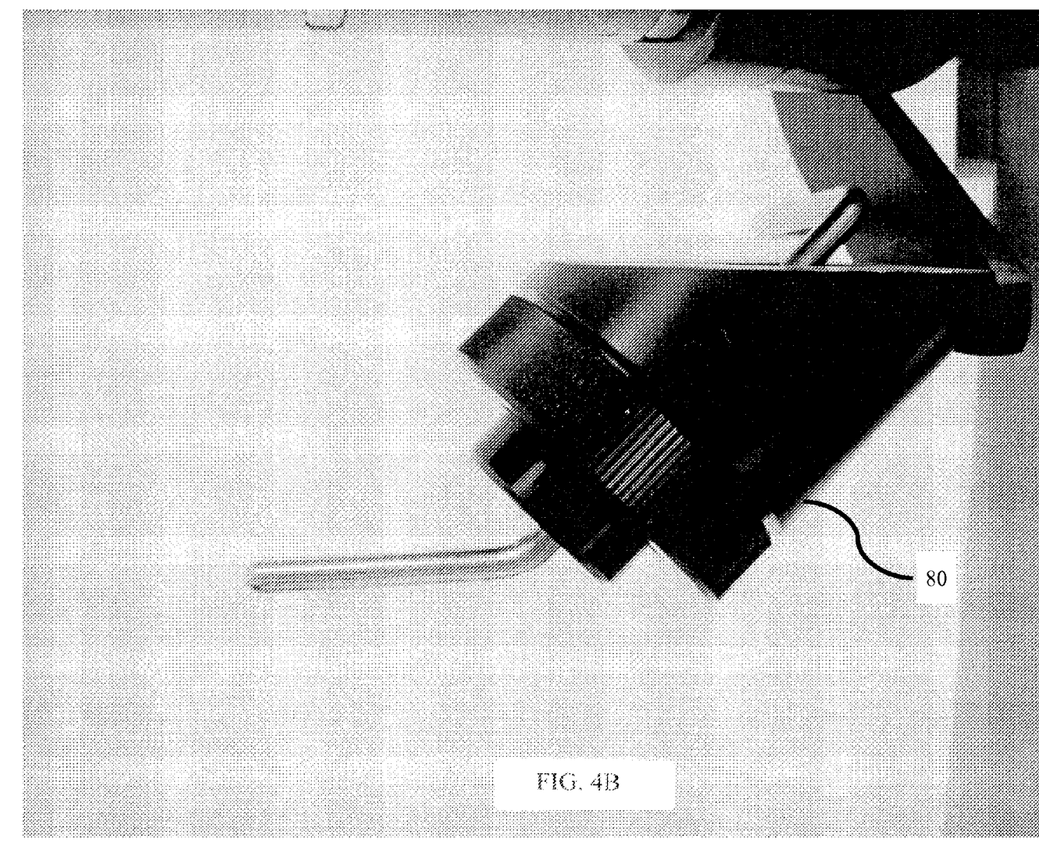
FIG. 4B—is a photograph of the right side view of the "joy stick" further enlarged to show details.
Figure 5:
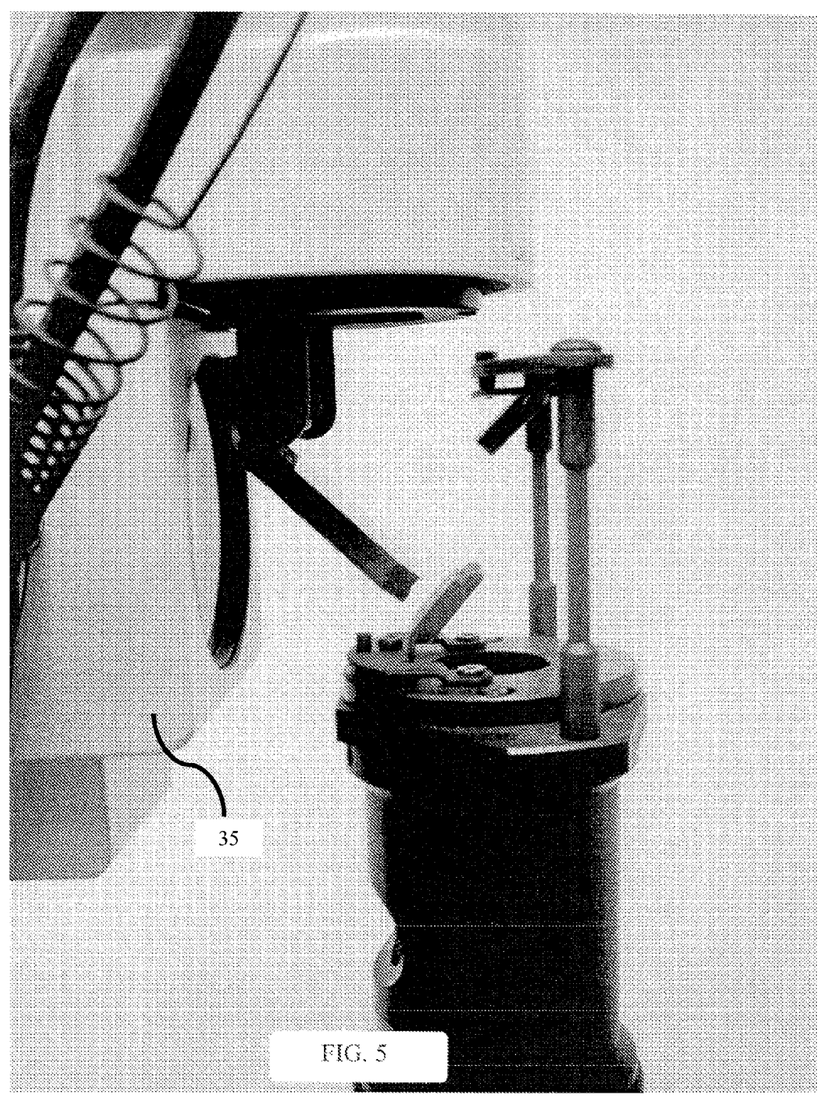
FIG. 5—is a photograph of the of the right side view of the slit lamp shown in FIG. 3, enlarged to show the details of one embodiment of an attached laser device.
Figure 6:
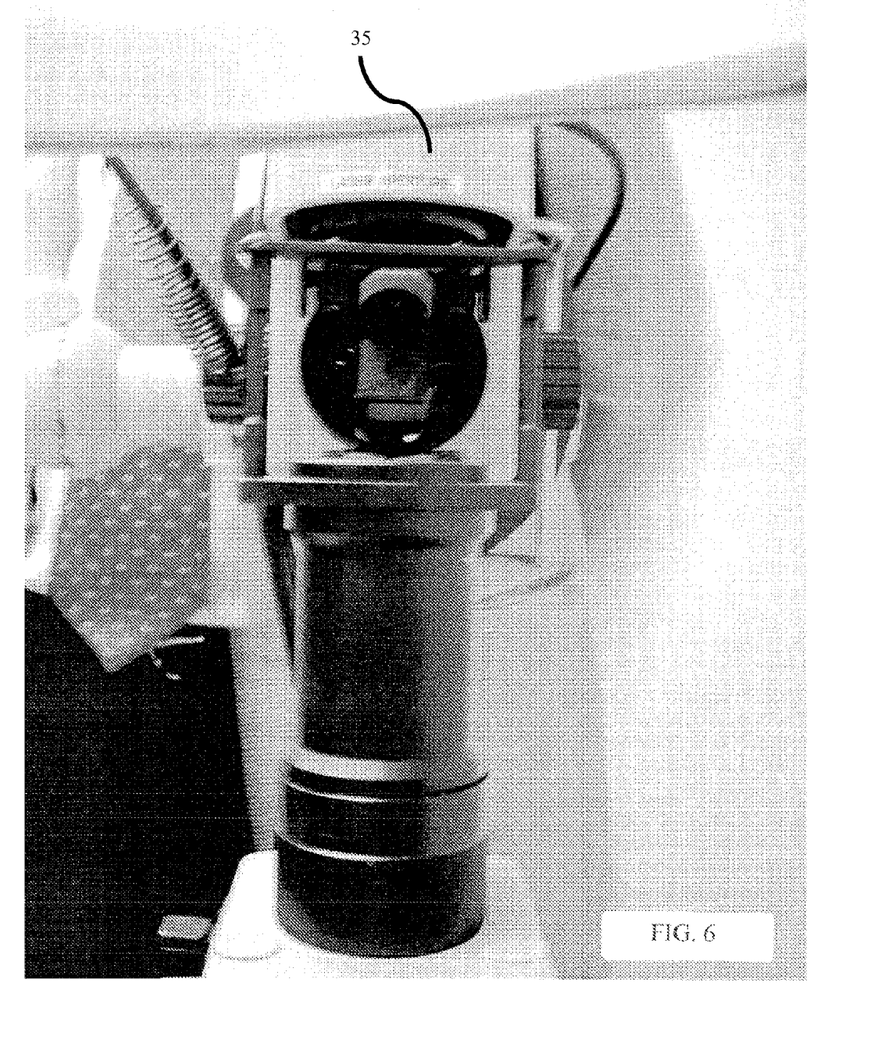
FIG. 6—is a photograph of the slit lamp shown in FIG. 3, as viewed from the back or patient side.
Figure 7:
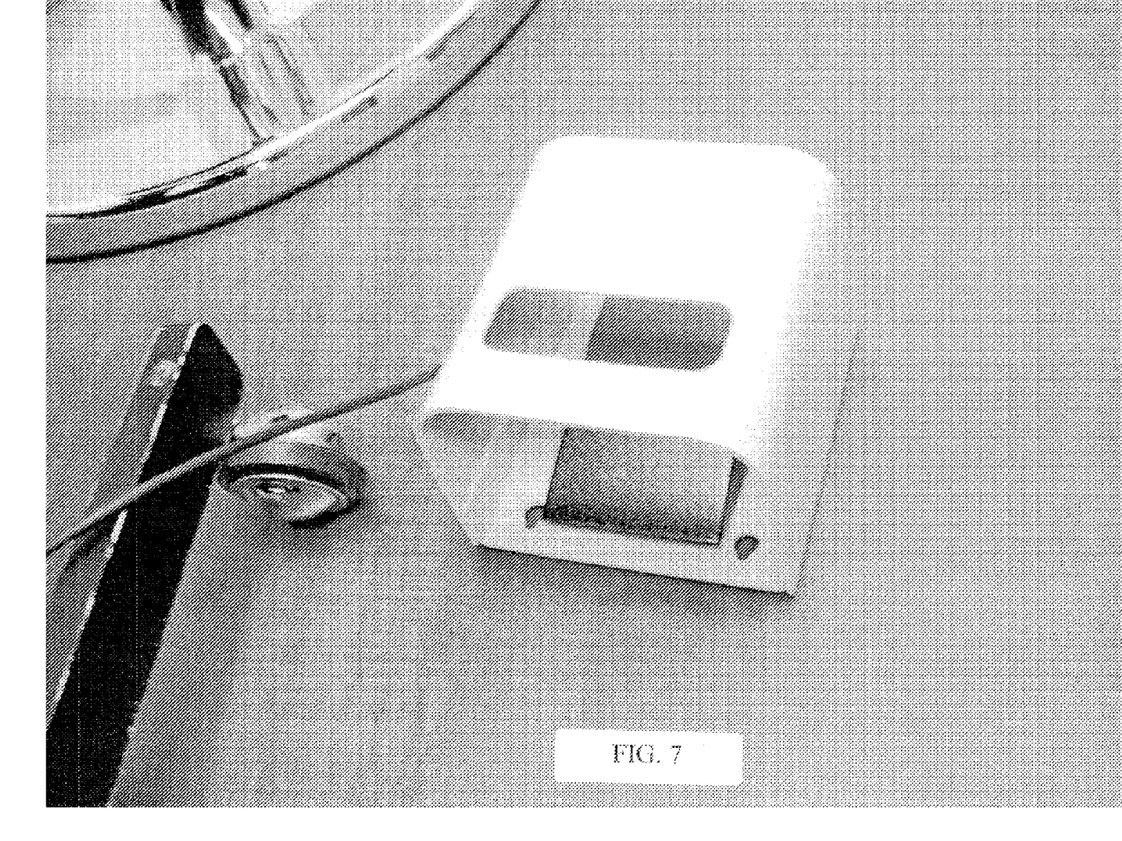
FIG. 7—is a photograph of one embodiment of a foot pedal used to control firing of a laser during a surgical procedure.
Figure 8:
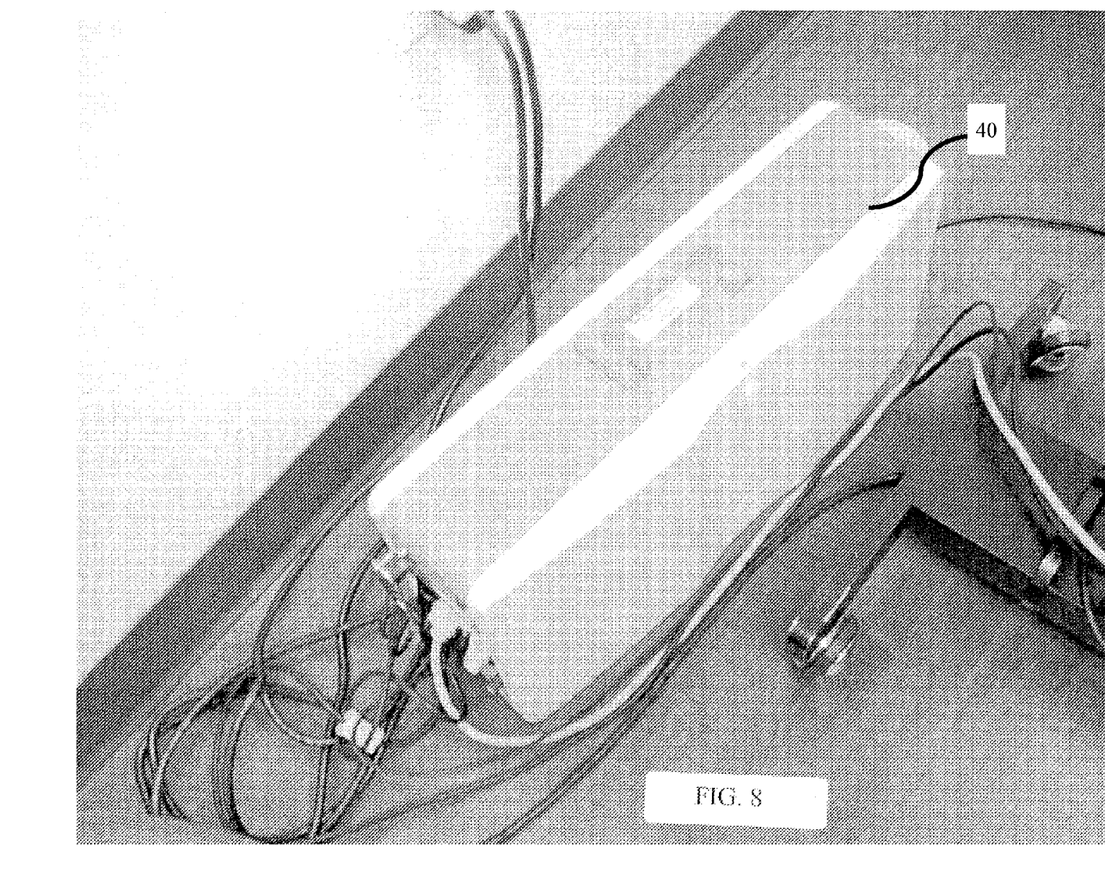
FIG. 8—is a photograph of an embodiment of one components of the subject invention.

In a preferred embodiment, shown for example in FIG. 2, a video camera 30 is connected to a secondary observation port 22 of a slit lamp 20 and the images are relayed through a computer 40 to a monitor screen 50. In a further preferred embodiment, the video camera 30 is a digitizing high-speed video imaging camera.

In many surgical procedures, including retinal surgery, it can be helpful to obtain one or more images of the enhanced tissue, such as a retina. For example, it is well-known in the art to use various dyes in the circulatory system to temporarily display the paths of arteries or veins, locate tumors, cancers, or other tissues. By way of example, in retinal surgery, it is common to obtain a fluorescein angiogram image (photograph) of a retina prior to a physician performing a procedure. To obtain a fluorescein angiogram, sodium fluorescein, a fast-acting, water-soluble dye, is injected into a patient's vein. Special camera filters can be used to photograph within certain light spectrums to create a high-contrast image. For example, in most fluorescein angiograms, special light filters allow only the green-yellow spectrum to be photographed creating a detailed high contrast image of a retina. By reviewing a fluoroscein angiogram, a physician or other specialist can observe a retina to determine whether the retina has abnormalities, damage, diseases, etc.

The tissues and structures observed in a fluoroscein image can then be correlated with the same tissue or structures in a real-time image of a retina, which can guide a physician to the appropriate area(s) for treatment, such as for laser coagulation. In a preferred embodiment, the subject invention advantageously provides a display of the fluoroscein image 60 and a real-time image 70 of a retina simultaneously. In a further preferred embodiment, the subject invention provides a display of a fluoroscein image 60 and a real-time image 70 overlaying and/or aligned with the other to produce a combined image 55.

The fluoroscein image 60 can be digitized by any of a variety of techniques well-known in the art, either at the time of taking the photograph or at a later time. Once digitized, a fluoroscein image 60 can then be displayed on numerous types of visual equipment. But, in a preferred embodiment, the image is displayed through a computer monitor 50. In a preferred embodiment, as shown, for example, in FIG. 2, a digitized fluoroscein image 60 is displayed by the same computer monitor 50 through which a real-time image 70, provided by a video camera 30, is also displayed. In a still further preferred embodiment, the fluoroscein image 60 and the real-time image 70 can be simultaneously displayed by the same monitor 50.

In a particularly preferred embodiment, the fluoroscein image 60, and any associated fiducial marks, indicators, etc. thereon, is aligned with the real-time image 70 to provide a physician with a combined image 55 on a computer monitor 50. Thus, during a procedure, a physician need only observe and direct attention to this combined and/or aligned computer image 55. This makes it easier for a physician to stay focused on the procedure instead of constantly re-directing their attention between two or more images and trying to mentally correlate positions during a procedure. This can increase the accuracy of a procedure and decrease surgery time.

The correlation of the images on a computer monitor 50 can be accomplished by any of a variety of techniques or procedures. For example, once the images are digitized they can be controlled by a computer. In this way, the images can be manually correlated or aligned using a mouse, joy stick, keyboard, etc. In a preferred embodiment, computer software is utilized to align the two or more images. The ability to use a computer and associated software and hardware, as known and/or readily developed by one skilled in the art advantageously allows the simultaneously displayed fluoroscein image 60 and the real-time image 70 to be more precisely correlated or overlaid such that the orientation of the real-time image 70 of a retina is substantially identical to the orientation of the same retina at the time the fluoroscein image 60 was obtained. During a surgical procedure, this aligned image 50 can further increase the accuracy of the procedure and decrease the surgery time.

In a still further preferred embodiment, computer software can be used to ensure that the images remain aligned, by correcting the position of the pre-surgical image(s) to compensate for movements in the real-time image(s) 70 (patient movements). Again, the advantageous ability to make such corrections can reduce procedural errors, thus increasing accuracy and decreasing surgery time.

During a procedure, a physician may find it useful or necessary to have one or more of the images dimmed or brightened, or to increase or decrease image resolution, change colors, display different fiducial marks or indicators, etc. Therefore, in another embodiment of the subject invention, one or more of the computerized images, or parts or features thereof, can be dynamically controlled or altered by various input devices of a computer, such as for example, keyboard, mouse, joy stick, touch-pads, voice- or noise-activated controls, etc.

In addition, medical or surgical devices and/or equipment often have position indicators, so that a physician knows where to direct the device during a procedure. For example, often in procedures utilizing a laser, a circle of light or an "aiming dot" correlated with the laser's position is displayed on the surface of a retina to visually indicate a laser 35 position prior to activation. In one embodiment, of the present invention, these indicators or aiming dots 36 can be displayed as part of the real-time image 70 of the retina. However, a person with skill in the art and benefit of the subject disclosure would be able to modify the display of these indicators such that they to can be computer controlled or altered as with the other images.

Figure 1:
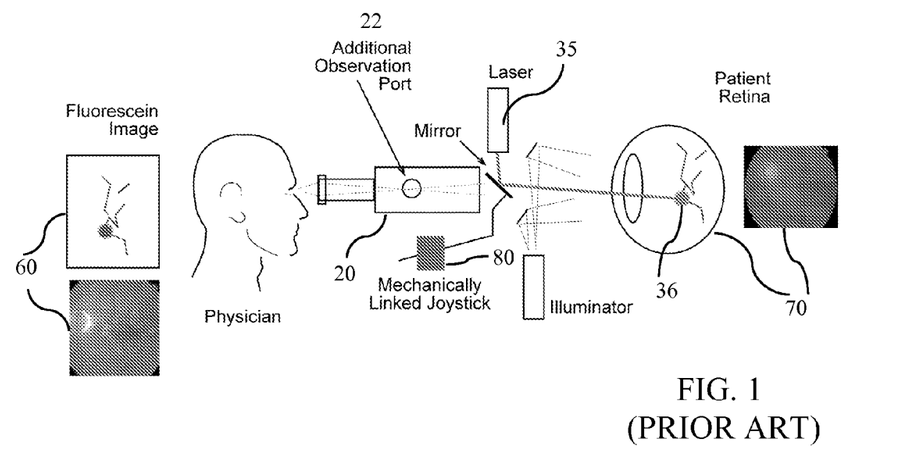

In a typical surgical procedure, a physician has direct control over administering or performing the actual procedure. Likewise, in most optical surgical procedures, such as, for example, an optical laser 35 surgery as shown in FIG. 1, physicians directly control where and how the procedure will be performed on a patient's eye(s). In surgeries using lasers, this is often accomplished by the use of a joy stick or similar device to control the laser by directing the aiming dot 36 of the laser to the appropriate area prior to activation of the laser. For some procedures, this direct, manual control is desired by physicians. In other procedures, such as for example, optical laser surgery, it is often required that physicians direct the laser and activate it at the appropriate points because there currently does not exist a way to automat such procedures.

Thus, a further advantage of the subject invention is the ability to automate certain procedures to be directed by computer control. A particular advantage of the subject invention is the ability to automate some or all of the optical laser surgical procedures. In a preferred embodiment, the surgical procedure or plan is programmed into a computer that has also been programmed to control the device or equipment, such as a joy stick 80, for administering the procedure. In a further embodiment, the location of one or more fiducial marks on a digitized flouroscein image 60 is programmed into and used to direct a computer to the appropriate target points. In a still further preferred embodiment, the computer is used to create fiducial marks or other indicators on an image, such as a fluoroscein image.

For example, in one embodiment of the subject invention, a physician can utilize one or more pre-surgical fluorescein images 60 and/or real-time images 70 of a retina to create a pre-surgical plan by marking on the image each point, fiducial mark, to which a laser can be directed and then activated. Upon digitizing the image, the pre-surgically planned fiducial marks can be programmed into a computer 40 to activate or deactivate one or more fiducial points. Computerized fiducial points can be used to direct a laser 35 to the appropriate treatment points.

In an alternative embodiment, the flouroscein image can be digitized and the computer used to insert one or more fiducial marks on the image, in addition to or instead of, fiducial marks placed on the pre-digitized image. In this way, fiducial marks can be made active or inactive, removed or added to the image, or otherwise manipulated as necessary. This allows a computer controlled laser 35 to be directed to appropriate In a still further embodiment, an optical laser is placed under computer control utilizing any of a variety of methods or devices well-known in the art. For example, optical laser devices 35 are often manipulated using a joystick 80 or similar device, as shown in FIG. 1. There are numerous devices, such as actuator devices 90, well-known in the art, capable of converting joystick 80 control to, for example, a keyboard, or, preferably, a mouse 95 control. Thus, utilizing a computer-programmed pre-surgical plan to control the position of, and activate, an optical laser, an optical surgical laser procedure can be automated.

In one embodiment, the computer-controlled optical laser can administer an entire procedure automatically. In this embodiment, the beam of a laser can be split by techniques known in the art in order to administer treatment to each desired point simultaneously. In a more preferred embodiment, a laser 35 is directed to and activated at each point separately. In alternative embodiments, the computer-controlled optical laser 35 procedure is administered in increments, wherein the laser 35 is directed to one or a few points, such that the physician is able to control various steps of the computer-controlled procedure. Even with some physician input, a computer-controlled optical laser surgery procedure can have increased accuracy and reduced surgery time.

In a further alternative embodiment, a physician can utilize a computer input device to control the rate at which an optical laser performs a procedure. For example, a physician can maintain control over when a computer moves to the next target point, thus ensuring that each target point during a procedure is adequately treated before moving to the next treatment point. In a still further alternative embodiment, a surgeon can utilize a computer mouse, or other computer input device, of any of a variety of types, to control the optical laser and perform a procedure utilizing the computers controls. In yet a further embodiment of the subject invention, a physician at some remote location, perhaps within the same facility, or a different geographical location, is able to utilize the computer images and computer-controlled devices and/or equipment to perform, direct, or oversee a procedure from said remote location.

The subject invention is particularly suited for use on existing slit lamps. Thus, a further embodiment of the subject invention comprises a kit containing the components necessary to retro-fit existing types of slit lamps to computer controlled monitor viewing. In a further embodiment, the kit can include one or more devices for converting manual control of various medical devices or equipment to computer control. In a still further embodiment, the kit can include software and/or devices for simultaneous viewing of two or more images, including the ability to align the images.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A system for viewing multiple images comprising:
   at least one digitized static image of tissue or a structure;
   a slit-limp apparatus for real-time observation of a tissue or structure;
   at least one digitizing apparatus connected to said slit-lamp apparatus for digitizing the real-time observation;
   a secondary display device capable of displaying the digitized static image overlapped and aligned with the real-time digitized image.

2. The system, according to claim 1, further comprising a medical apparatus for administering a treatment or procedure utilizing the simultaneous display of the digitized images.

3. The system, according to claim 2, wherein said medical device is an optical laser.

4. A method for viewing multiple images wherein said method comprises the use of a device having:
   slit-lamp apparatus for real-time observation of a tissue or structure;
   at least one digitizing apparatus connected to said slit-lamp apparatus for digitizing the real-time observation; and
   a secondary display device capable of displaying digitized images, said method comprising obtaining a digitized static image of a tissue or structure; obtaining a real-time digitized image of a tissue or structure; simultaneously displaying the digitized static image overlapped and aligned with the digitized real-time observation image on the secondary display device.

5. The method, according to claim 4, wherein said method is used in the performance of surgery.

6. The method, according to claim 5, wherein the surgery is performed with a laser.

7. The method, according to claim 4, wherein a dye is used to facilitate obtaining an image of a tissue.

8. The method, according to claim 7, wherein the dye is fluoroscein.

9. The method, according to claim 4, further comprising the use of software to facilitate maintaining alignment of the images during the course of a surgical procedure.

10. The method, according to claim 6, wherein the surgery is on a retina.

11. The method, according to claim 4, which is used for laser surgery of the eye and wherein at least some of the laser procedure is automated.

12. The method, according to claim 4, wherein fiducial marks are used to direct a laser during surgery.

13. The method, according to claim 4, wherein said method is used to perform surgery and wherein a surgeon performing the surgery is at a location remote from the location of the patient.

14. A kit for performing an optical surgical procedure, the kit comprising:
   (a) at least one digitized static image of a tissue or a structure;
   (b) a device comprising,
      (i) a slit-lamp apparatus for real-time observation of a tissue or structure; and
      (ii) at least one digitizing apparatus connected to said slit-lamp for digitizing the real-time observation;
   (c) a secondary display device capable of simultaneous display of the overlapped and aligned static and real-time digitized images;
   (d) an optical laser device; and
   (e) a computer capable of at least partially controlling the operation of the optical laser device such that the optical surgical procedure can be at least partially automated.

\* \* \* \* \*